United States Patent [19]

Tramontano et al.

[11] Patent Number: 4,659,567
[45] Date of Patent: Apr. 21, 1987

[54] MOLECULES WITH ANTIBODY COMBINING SITES THAT BIND TO HYDROLYTIC TRANSITION STATES

[75] Inventors: Alfonso Tramontano; Richard A. Lerner, both of La Jolla, Calif.

[73] Assignee: Scripps Clinic & Research Foundation, La Jolla, Calif.

[21] Appl. No.: 648,406

[22] Filed: Sep. 7, 1984

[51] Int. Cl.$^4$ .......................... A61K 39/00; C07F 9/40; C07F 9/65; C07D 209/48
[52] U.S. Cl. ..................................... 424/85; 436/547; 549/220; 549/289; 548/462; 548/465; 548/415; 435/814; 435/19; 435/196; 558/193
[58] Field of Search ............... 260/112 B, 112 R, 944, 260/942; 424/85; 436/547, 548; 549/220, 289; 548/462, 465, 415; 435/814

[56] References Cited

U.S. PATENT DOCUMENTS

| | | | |
|---|---|---|---|
| 3,641,147 | 2/1972 | Taplias | 548/465 |
| 3,733,379 | 5/1973 | Szabo | 260/942 |
| 3,876,666 | 4/1975 | Oswald et al. | 549/289 |

Primary Examiner—John Kight
Assistant Examiner—Garnette D. Draper
Attorney, Agent, or Firm—Dressler, Goldsmith, Shore, Sutker, Milnamow Ltd.

[57] ABSTRACT

A phosphonamidate or phosphonate analog-ligand having a conformation that substantially corresponds to the conformation of a hydrolytic transition state of an amide or ester ligand is used to produce antibodies of predetermined specificity. The antibodies include an epitope that binds to and thereby stabilizes the tetrahedral carbon atom of the amide or ester hydrolysis transition state of the ligand to hydrolyze the ligand at a predetermined site.

10 Claims, 2 Drawing Figures

MOLECULES WITH ANTIBODY COMBINING SITES THAT BIND TO HYDROLYTIC TRANSITION STATES

DESCRIPTION

1. Technical Field

The present invention relates to antibodies, antigens and immunogens, and more particularly to molecules that contain an epitope that binds to and thereby stabilizes the tetrahedral carbon atom of an amide or ester hydrolysis transition state.

2. Background of the Invention

Binding phenomena between ligands and receptors play many crucial roles in bioloqical systems. Exemplary of such phenomena are the binding of oxygen molecules to deoxyhemoglobin to form oxyhemoglobin, and the binding of a substrate to an enzyme that acts upon it such as between a protein and a protease like trypsin. Still further examples of biological binding phenomena include the binding of an antigen to an antibody, and the binding of complement component C3 to the so-called CR1 receptor.

Many drugs and other therapeutic agents are also believed to be dependent upon binding phenomena. For example, opiates such as morphine are reported to bind to specific receptors in the brain. Opiate agonists and antagonists are reported to compete with drugs like morphine for those binding sites.

Ligands such as man-made drugs, like morphine and its derivatives, and those that are naturally present in biological systems such as endorphins and hormones bind to receptors that are naturally present in biological systems, and will be treated together herein. Such binding may lead to a number of the phenomena of biology, including particularly the hydrolysis of amide and ester bonds as where proteins are hydrolyzed into constituent polypeptides by an enzyme such as trypsin or papain, or where a fat is cleaved into glycerine and three carboxylic acids, respectively.

Hydrolysis of amide and ester bonds is thought by presently accepted chemical theory to proceed in aqueous media by a reaction at the carbonyl carbon atom to form a transition state that contains a tetrahedral carbon atom bonded to (a) a carbon atom of the acid portion of the amide or ester, (b) two oxygen atoms, one being from the carbonyl group and the other from a hydroxyl ion or water molecule of the medium, and (c) the oxygen atom of the alcohol portion of an ester or the nitrogen atom of the amine portion of an amide. Transition states of such reactions are useful mental constructs that by definition, cannot be isolated, as compared to intermediates, which are isolatable.

Although the above hydrolytic transition states can not be isolated, a large amount of scientific literature has been devoted to the subject. Some of that literature is discussed hereinafter.

While the before-described transition state for amide and ester hydrolyses is believed to be well understood, the parameters of the topology, e.g., size, shape and charge, of receptor binding sites in which particular amides, such as proteins, or esters, such as fats, react through those transition states is not as well understood. It would therefore be beneficial if the topology of a plurality of binding sites were known so that the interactions of the ligands that bind in those sites could be studied. Unfortunately, the topology of receptor binding sites in biological hydrolyses is generally unknown, except for a relatively small number of enzymes whose X-ray crystal structures have been determined.

This lack of knowledge of binding site topology stems in part from a lack of knowledge of even the location in cells of many binding sites of receptors. In addition, for those receptor binding sites whose location is known, the chemical identity; i.e., protein and carbohydrate composition, of the binding site is generally unknown. Thus, the investigator is generally stymied in seeking to understand the topological requirements of receptor binding sites and therefore in seeking to construct therapeutic agents that can fulfill those requirements.

Investigators must therefore screen potential therapeutic agents in animal or cell culture studies to ascertain whether a potential therapeutic agent may be useful. Such systems, while useful, are expensive and time-consuming to use.

Even where the topology and chemical reactivity of a hydrolytic receptor such as an enzyme are known, enzymes such as hydrolytic proteases typically cleave their substrates, polypeptide chains, adjacent to a particular amino acid residue that may occur several times in the protein's polypeptide chain. While such relatively random cleavage can be useful in obtaining a polypeptide map of the protein, that relatively random cleavage is not as useful where particular amino acid residue sequences are desired to be produced.

For example, modern genetic engineering techniques have been useful in preparing fusion proteins that contain a desired protein or polypeptide fused to the transcription product of a vector gene such as the lac z gene. The use of such fusion proteins is, however, hindered by the presence of fragments of the vector gene product. It would also therefore be beneficial if proteolytic enzyme-like molecules could be developed that would cleave such fusion products between the wanted and unwanted fusion polypeptide or protein portions.

BRIEF SUMMARY OF THE INVENTION

The present invention contemplates a molecule that contains an antibody combining site or idiotype-containing polyamide, referred to also as a receptor, that binds to the hydrolytic transition state of an ester or amide ligand. The ligand transition state so bound contains a tetrahedral carbon atom bonded to (a) a carbon atom, (b) two oxygen atoms, and (c) the oxygen atom of an ester or the nitrogen atom of an amide.

Molecules containing the idiotype to the hydrolytic transition state of a ligand are raised or induced by immunizing analog-ligand molecules containing an analog of a hydrolytic transition state as the epitope. The immunizing analog-ligand hydrolytic transition state molecule contains a tetrahedrally bonded central atom bonded directly to (a) a carbon atom of the acid portion of the analogous ligand amide or ester, (b) two oxygen atoms and (c) a third oxygen atom or a nitrogen atom, the third oxygen atom or nitrogen atom being bonded to a carbon atom of an analogous ester or amide of the ligand.

The carbon atom, (a) above, bonded directly to the central tetrahedral atom of the analog-ligand molecule, is included in a chain that contains at least 5 atoms, and more preferably about 15 atoms, as is the third oxygen or nitrogen atom, (c) above. Of the two oxygen atoms, (b) above, bonded directly to the central atom, one oxygen atom (i) is bonded twice in an oxo group to the central atom, (ii) is part of an hydroxyl group or (iii) is the oxygen of an alkoxy group containing a $C_1$–$C_4$ lower alkyl group. This oxygen and its second bond to the central atom or another group is referred to as —$OR_4$. The second oxygen bonded to the central atom is an —$OR_2$ group wherein $R_2$ is selected from the group consisting of hydrogen (H), a $C_1$–$C_4$ lower alkyl and an amino-terminal- and carboxyl-terminal-protected serine residue. The fourth atom, (c) above, bonded to the central atom of the analog-ligand molecule is the alcohol oxygen atom of an ester or the amine nitrogen atom of an amide of the analogous ester or amide of the ligand. That fourth atom is a portion of a chain that contains at least 5, and more preferably 15 atoms, and with the remainder of the chain constitutes $R_3$. The tetrahedrally bonded central atom is preferably phosphorus.

It is thus seen that the invention contemplates ligands and analog-ligands containing an analog to the hydrolytic transition state of the ligand. Those molecules differ in the fact the ligand contains a carbonyl group of an amide or ester while the ligand-analog contains a non-carbon central atom such as phosphorus. The ligand and analog-ligand may also differ in the substitution of the two oxygen atoms (b) bonded to the central atom since the analog-ligand must possess sufficient stability to be used as a hapten, while the transition state mimicked by the analog-ligand cannot be isolated.

Exemplary immunizing analog-ligand molecules that contain an analog of a hydrolytic transition state are represented by the formula:

wherein $R_1$ is $R_2$ is H;

$R_3$ is $R_4$ is (i) a second bond between the oxygen and central phosphorous atom, (ii) hydrogen or (iii) $C_1$–$C_4$ alkyl; and Y is O or NH.

The analog-ligand hydrolytic transition state molecules are themselves ligands and are also contemplated in this invention. These ligand molecules are of relatively small molecular size and are therefore typically linked to a larger, carrier molecule. Such relatively small molecules are commonly referred to as haptens. These analog-ligand molecules also typically contain a linking atom or group such as a reactive mercaptan that provides a means to attach the haptenic analog-ligand molecules to carriers for use as immunogens.

The antibody combining site-containing molecules of the present invention are themselves receptors or receptor models and provide information on the conformational preferences of antibody-hapten interactions through study of the intramolecular reactivity patterns of receptor-ligand complexes that are formed between the antibody combining site-containing molecules (receptors) and ligands of differing structures that contain similar or identical epitopic regions.

A method of preparing polyclonal receptor molecules that bind to the hydrolytic transition state of a particular amide or ester is also contemplated. Here, a before-described haptenic analog-ligand molecule containing a hydrolytic transition state analog is provided linked to a carrier as an immunogenic conjugate. The conjugate thus provided is dissolved or dispersed in a physiologically tolerable diluant to form an inoculum. The inoculum is introduced as by injection into a mammalian host in an amount sufficient to induce antibodies to the haptenic analog-ligand. The antibodies so induced are harvested. The harvested antibodies that immunoreact with the immunizing, haptenic analog-ligand are then collected.

In particularly preferred practice, monoclonal antibodies are prepared. Here, the above immunizing technique is used and the harvested antibodies are assayed for their ability to bind to (immunoreact with) the immunizing, haptenic ligand analog. Immunoglobulin-producing cells such as those from the spleen of an animal whose antibodies bind to the immunizing, haptenic analog-ligand are collected and are fused with myeloma cells to form hybridoma cells. The hybridoma cells are grown in a culture medium and the supernatant medium from the growing hybridoma cells is assayed for the presence of antibodies that bind to the immunizing, haptenic analog-ligand. Hybridoma cells whose supernatant contains such binding antibodies are then cloned to provide the desired monoclonal antibodies from culture medium supernatant or from the ascites of a host mammal into which the hybridoma is introduced.

The described polyclonal or monoclonal antibodies may be used as the receptors of this invention. Alternatively, the so-called Fc or Fc' portions of the antibodies may be removed as by enzymic cleavage to provide an antibody combining site (idiotype-containing polyamide) that binds to the immunizing, haptenic analog-ligand such as Fab or F(ab')₂ antibody portion, respectively.

The polyclonal, monoclonal and idiotype-containing polyamide receptors also bind to the hydrolytic transition state of the amide or ester ligand. Such binding typically leads to hydrolysis of the ligand.

The present invention provides several benefits and advantages. One benefit is the preparation of receptors whose binding site topological requirements are tailored to a hydrolyzable ligand to be studied.

Another benefit of the present invention is the preparation of receptors that hydrolyze the amide or ester ligand at a predetermined site.

An advantage of the invention is that because of the specificity of the hydrolyzing receptors that may be produced, a ligand containing a plurality of different hydrolyzable bonds such as a polypeptide or protein may be hydrolyzed at a preselected, particular hydrolyzable bond.

Yet another advantage of the present invention is the provision of receptors that bind to the hydrolytic transition state of a particular, preselected ligand, thereby providing a means for studying the hydrolysis reaction of that ligand.

Still further benefits and advantages of the present invention will be apparent to those skilled in the art from the disclosures that follow.

BRIEF DESCRIPTION OF THE DRAWINGS

In the drawings, which constitute a portion of this disclosure.

DETAILED DESCRIPTION OF THE INVENTION

I. Introduction

The present invention relates to the production of antibodies and idiotype-containing polyamide (antibody combining sites) induced by analogs that mimic the conformation of chemical intermediates in the reaction sequence for the hydrolysis of an ester or an amide. The antibodies and idiotype-containing polyamides bind to the hydrolytic transition state of a preselected portion of a ligand.

Antibodies and enzymes are both proteins whose function depends on their ability to bind specific target molecules. Enzymatic reactions differ from immunological reactions in that in an enzymatic reaction the binding of the enzyme to its substrate typically leads to chemical catalysis, while a non-catalytic complex is the usual result of antibody-antigen binding.

Enzymes are believed catalyze the hydrolysis of proteins by combining with the protein to stabilize the transition state of the hydrolysis reaction. It is generally believed that the rate of an enzymatic reaction is increased relative to the rate of a non-enzymatic reaction because of the ability of the enzyme to stabilize the reaction's transition state; i.e., to reduce the free energy of the transition state, and thus, the free energy of activation, of the reaction [Jencks, W. P., Adv. Enzymology, 43, 219 (1975) and Pauling, L., Amer. Scientist, 36, 58 (1948)]. It is further thought that the enzyme accomplishes this lowering of the reaction free energy by binding the reactant's transition state geometry more strongly than it binds to the corresponding substrate(s) or product(s).

This means that the intrinsic binding energy of the enzyme is much greater than can be measured from the binding of substrates or products. Essentially, the binding energy of the enzyme is utilized to perform the chemical reaction [Jencks, W. P., XVII International Solvay Conference (November 1983)].

The basic idea behind immunological hydrolysis described herein contemplates the preparation of antibodies of predetermined specificity that preferentially bind to and thereby stabilize the transition state of amide or ester bond hydrolysis upon binding to the specified ligand.

Such preferential binding and stabilization results in a reduction in the activation energy for the hydrolysis reaction, thus meeting a criterion for catalysis. Antibodies that display this property may be obtained by immunization with synthetic analogs that are chemically modified to resemble the bonding characteristics of a substrate ligand undergoing bond hydrolysis; i.e., by immunization with transition state analogs of the particular reaction.

The mechanism by which an antibody hydrolyzes an ester or amide bond of a bound ligand can be thought of in terms of an "induced fit" model. As the loosely bound substrate distorts or rearranges to conform to the binding geometry of the antibody, stress can be relieved by chemical reorganization of a single, predetermined amide or ester bond such that this reorganization leads to the hydrolysis of the bond.

The term "receptor" is used herein to mean a biologically active molecule that binds to a ligand, or analog-ligand. The receptor molecules of the present invention are antibodies, substantially intact antibodies or idiotype-containing polyamide portions of an antibody. Biological activity of a receptor molecule is evidenced by the binding of the receptor to its antigenic ligand or analog-ligand upon their admixture in an aqueous medium, at least at physiological pH values and ionic strengths. Preferably, the receptors also bind to the antigenic ligand within a pH value range of about 5 to about 9, and at ionic strengths such as that of distilled water to that of about one molar sodium chloride.

Idiotype-containing polyamide portions (antibody combining sites) of antibodies are those portions of antibody molecules that include the idiotype, and bind to the ligand or analog-ligand. Such portions include the Fab, Fab' and F(ab')₂ fragments prepared from antibodies by well-known enzymatic cleavage techniques. See for example, U.S. Pat. No. 4,342,566 to Theofilopoulos and Dixon. Inasmuch as the antibodies from which idiotype-containing polyamides are obtained are described as raised against or induced by immunogens, idiotype-containing polyamide receptors will also be discussed as being "raised" or "induced" with the understanding that a cleavage step is required to obtain an idiotype-containing polyamide from an antibody. Intact antibodies are preferred, however, and will be utilized as illustrative of the receptor molecules of this invention.

The receptors useful in the present invention are preferably monoclonal antibodies. A "monoclonal antibody" is a receptor produced by clones of a single cell called a hybridoma that secretes but one kind of receptor molecule. The hybridoma cell is fused from an antibody-producing cell and a myeloma cell or other self-perpetuating cell line.

Techniques for preparing the monclonal antibodies of the present invention are well known. Such receptors were first described by Kohler and Milstein, *Nature,* 256, 495 (1975), which is incorporated herein by reference. Monoclonal antibodies are typically obtained from hybridoma tissue cultures or from ascites fluid obtained from mammals into which the hybridoma tissue was introduced. Both methods are described herein.

As described herein, chemical analogs of ester ligands have been synthesized that incorporate phosphonamidate or phosphonate moieties at specific, predetermined sites to mimic the conformation of the transition state in the hydrolysis of an amide or ester bond. Such analogs are suitable candidates for this investigation because it is known that phosphonamidates have been used as transition state analogs in the inhibition of proteolytic enzymes [Bartlett, et. al., *Biochemistry,* 22, 4618 (1983)].

Hydrolysis of the amide bond of polypeptides or proteins requires analog-ligands that are substantially free from hydrolysis when utilized as a haptenic immunogen. Phosphonamidates described for the inhibition of certain proteases (Bartlett et al., id. and Jacobsen et al., *J. Am. Chem. Soc.,* 103, 654 (1981) can also be modified for inducing the production of useful receptors herein.

Short polypeptide chains can induce the production of antibodies that recognize and bind to the protein at a predetermined specific site. The present invention carries the earlier work with polypeptides a major step forward. Here, the antibodies (receptors) are induced by an immunizing haptenic first molecule (the analog-ligand), and recognize and bind not only to that first molecule, but also to a second, related molecule (the ligand). In binding that second molecule, the receptor causes hydrolysis of a preselected, ester or amide bond that corresponds in topology to the topology of the immunizing, haptenic first molecule. The correspondence in topology; i.e., size, shape and charge, provides a means for preselecting the site at which hydrolysis of the ligand occurs.

Consequently, by synthesis of a relatively small, immunizing haptenic analog-ligand, one may induce the production of receptor molecules that recognize, bind to and cause hydrolysis of an ester or amide bond in a larger molecule that may contain a plurality of hydrolyzable amide or ester bonds that are stable to hydrolysis caused by the receptor. Thus, a receptor may be prepared that causes hydrolysis of a selected, predetermined amide bond of a protein or polypeptide such as the before-discussed genetically engineered fusion protein.

The implication of this result is that one may confer the activity of hitherto unknown proteases to immunoglobulins.

Furthermore, the activity of the antibody may be directed to any predetermined site at will by designating the amide bond to be cleaved with the phosphonamidate configuration in the haptenic analog-ligand used for immunization.

Thus a method is described for the selective proteolysis of a protein whose local sequence conforms to that of the polypeptide targeted. The applications of such a method in protein chemistry, biochemistry, and medicine are without limit.

The following discussion relates in part to the hydrolysis of p-nitrophenyl and coumarinyl esters. Compounds C1 and C4 were prepared to act as the transition state analogs of, for example, the corresponding p-nitrophenyl and coumarinyl carbon rather than phosphorus esters in an immunological study. Antibodies generated, to Compound C1 bound to a carrier, were isolated and screened in an assay for hydrolysis of the ligand ester that corresponds to analog-ligand Compound C1. The liberation of the fluorescent 4-methylumbelliferone molecule in this reaction was used to facilitate the detection of hydrolytically active antibodies. Such antibodies did in fact hydrolyze coumarin esters.

The antibodies and idiotype-containing polyamide portions of antibodies of this invention are induced by a haptenic ester or amide analog-ligand hydrolytic transition state molecule. This haptenic molecule contains a tetrahedrally bonded central phosphorus or silicon atom bonded directly to (a) a carbon atom, (b) two oxygen atoms and (c) a third oxygen atom or a nitrogen atom, the third oxygen atom or nitrogen atom being bonded to a carbon atom of an analogous ester or amide of the ligand.

The carbon atom, (a) above, bonded directly to the central tetrahedral atom of the analog-ligand molecule, is included in a chain that contains at least 5 atoms, and more preferably about 15 atoms that is referred to in the general formula below as $R_1$. The two oxygen atoms, (b) above, bonded directly to the central atom are defined in that general formula by $-OR_2$, and $-OR_4$, where $R_2$ is selected from the group consisting of hydrogen (H), a $C_1-C_4$ lower alkyl group and an amino-terminal-protected and carboxyl-terminal-protected serine residue, and where $R_4$ is selected from the group consisting of the second bond of an oxo group ($=O$) bonded to the central atom, hydrogen (H) and a $C_1-C_4$ lower alkyl group. The fourth atom, (c) above, bonded to the central atom is the alcohol oxygen atom of an ester or the amine nitrogen atom of an amide of the analogous ester or amide of the ligand, and is also a portion of a chain containing at least 5, and more preferably 15 atoms. This fourth atom bonded directly to the central, tetrahedral atom and its accompanying chain are defined in the general formula as $R_3$.

The general formula for the haptenic, analog-ligand molecule may be illustrated as follows:

wherein P is the tetrahedrally bonded central phosphorous atom, and $R_1$, $R_2$, $R_3$ and $R_4$ are defined hereinbefore.

In preferred practice, $R_2$ is H so that $OR_2$ is OH, and $R_4$ is a second bond so that $OR_4$ is $=O$ (oxo).

In particularly preferred practice, $R_1$ is a radical selected from the group consisting of:

Each of the haptenic ligand hydrolytic transition state analogs corresponds to an amide or ester in which a carbonyl-containing —C(O)—O— or —C(O)—NH— group replaces the central atom of the transition state analog and its four bonded atoms. The correspondence between the ligand and analog-ligand is shown below for five pairs of molecules with the understanding that the contemplated ligands and analog-ligand containing hydrolytic transition state analogs bear the same structural relationship as do the illustrated pairs of molecules.

Particularly preferred $OR_3$ groups are selected from the group consisting of:

| Ligand | Ligand Hydrolytic Transition State Analog |
|---|---|

II. Synthesis of Ligand Hydrolytic Transition State Analogs

Preparation of C1 Analog-Ligand
[N-(benzyloxycarbonyl)-p-aminobenzyl]-p-nitrophenyl phosphonate

Figure 1:
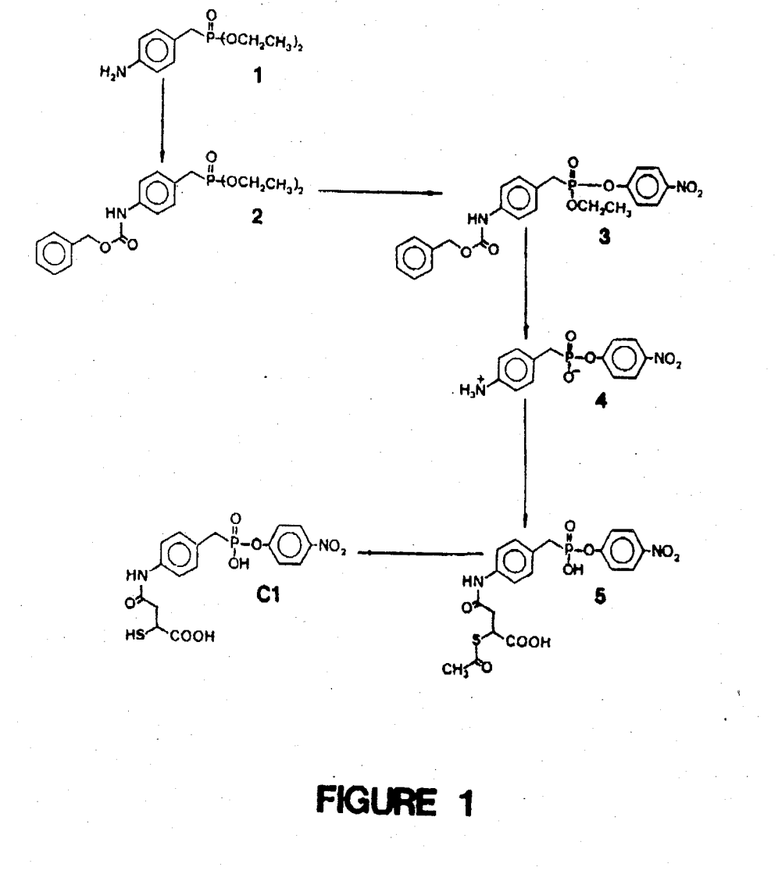
FIG. 1 illustrates a schematic reaction sequence in the synthesis of the compound designated "C1"- [N-(benzyloxycarbonyl)-p-aminobenzyl]-p-nitrophenyl phosphonate.
Figure 2:
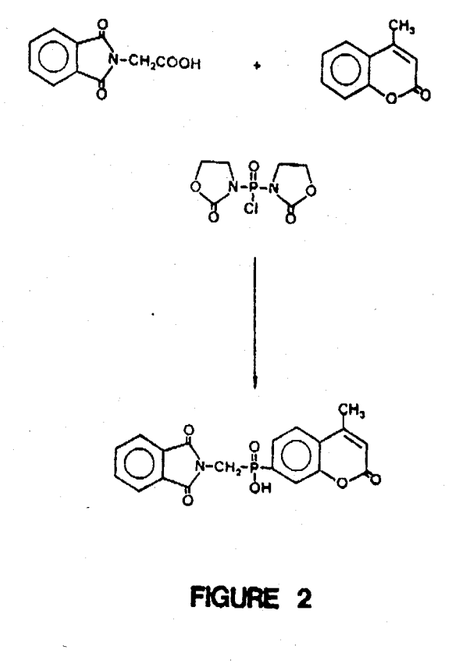
FIG. 2 illustrates a schematic reaction sequence in the synthesis of the compound designated "C4".

The parenthesized numerals 1 through 5 in the discussion below refer to intermediates shown in FIG. 1.

Diethyl p-aminobenzylphosphonate (1) (Aldrich Chemical Co., Milwaukee, WI) was converted to the p-carbobenzyloxy derivative (2) by the addition of 1.2 equivalents benzyl chloroformate in saturated aqueous sodium bicarbonate (NaHCO$_3$) for 20 minutes at 23° C. That derivative was treated with 1.1 equivalents phosphorous pentachloride (PCl$_5$) in chloroform at 50° C. for 2 hours. Pyridine (5 equivalents) and p-nitrophenol (3 equivalents) were added at 23° C. and subsequent workup provided the ethyl p-nitrophenyl phosphonate (3).

The cleaved ester and carbobenzyloxy group were cleaved simultaneously by treatment of a solution of 3 in acetonitrile with sodium iodide and trimethylsilyl chloride (5 equivalents each) for 6 hours at 50° C.

The reaction was quenched with methanol. After removal of all solvent, the amino acid (4) was extracted into 20 percent aqueous acetic acid and the aqueous solution was washed several times with ether. The aqueous solution was made basic with sodium bicarbonate and treated with S-acetylmercaptosuccinic anhydride (10 equivalents) at 23° C. for one hour. The solution was acidified with concentrated HCl (to pH 3) and was extracted with n-butanol to provide the diacid (5). The thiol group was liberated by treatment of an aqueous solution of 5 with sodium hydroxide to raise the pH to 9. The solution was then buffered with acetic acid to pH 5 and was used as such to prepare the KLH conjugate.

Preparation of C1 Ligand
Coumarin ester of p-acetamidophenylacetate

A mixture of p-aminophenylacetic acid and acetic anhydride (5 equivalents) in 10 percent aqueous sodium bicarbonate was stirred for 30 minutes at room temperature. The solution was acidified with HCl and was extracted with methylene chloride. p-Acetamidophenyl acetic acid (1 equivalent) was condensed with 4-methyl-umbelliferone (1.5 equivalents) in methylene chloride with dicyclohexylcarbodiimide (2 equivalents) and triethylamine (2 equivalents). The resulting solution was diluted with ethyl acetate and washed with dilute HCl. The organic layer was concentrated and C1 was isolated therefrom. The product was characterized as C1 by NMR and by the production of a single spot upon thin layer chromatography.

Preparation of C4 Analog-Ligand n-Phthaloyl glycine (1 equivalent) and 4-methyl-umbelliferone (1 equivalent) in methylene chloride were treated with 1.5 equivalents of Bis-oxazolidinyl-phosphonochlorate. Triethylamine (1.5 equivalents) was added and the solution was stirred for 3 hours at room temperature.

The reaction mixture was diluted with methylene chloride and was washed with 0.5 Molar aqueous HCl. The organic layer was concentrated and C4 was characterized by NMR and the production of a single spot upon thin layer chromatography.

Preparation of C4 Ligand n-Phthaloyl glycine (1 equivalent) was condensed with 4-methyl-umbelliferone (1 equivalent) in methylene chloride with dicyclohexylcarbodiimide (2 equivalents) and triethylamine (2 equivalents). The resulting solution was diluted with ethyl acetate and washed with dilute HCl. The organic layer was concentrated and the C4 ligand was isolated therefrom. The product was characterized by NMR and by the production of a single spot upon thin layer chromatography.

III. Coupling of Compounds to Protein Carriers

Conjugates of the above prepared haptenic analog-ligand molecules with the carrier keyhole limpet hemocyanin (KLH) were prepared by activation of KLH with MBS (m-maleimidobenzoyl-N-hydroxy succinimide ester), and coupling to the thiol group of compounds C1-C5. See, for example, Liu et al., Biochem., 80, 690 (1979).

Useful carriers are well known in the art and are generally proteins themselves. Exemplary of such carriers are keyhole limpet hemocyanin (KLH), edestin, thyroglobulin, albumins such as bovine serum albumin or human serum albumin (BSA or HSA, respectively), red blood cells such as sheep erythrocytes (SRBC), tetanus toxoid, cholera toxoid as well as polyamino acids such as poly(D-lysine:D-glutamic acid), and the like.

As is also well known in the art, it is often beneficial to bind a compound to its carrier by means of an intermediate, linking group. According to the present invention, the intermediate linking group is preferably an m-maleimidobenzoyl N-hydroxysuccinimide ester (MBS). MBS is typically first added to the carrier by an ester-amide interchange reaction. Thereafter, the above Michael reaction can be followed, or the addition can be followed by addition of a blocked mercapto group such as thiolacetic acid ($CH_3COSH$) across the maleimido-double bond. After cleavage of the acyl blocking group, and a disulfide bond is formed between the deblocked linking group mercaptan and the mercaptan of the thiol group of the compound.

The choice of carrier is more dependent upon the ultimate intended use of the antigen than upon the determinant portion of the antigen, and is based upon criteria not particularly involved in the present invention. For example, if the conjugate is to be used in animals, a carrier that does not generate an untoward reaction in the particular animal should be selected. If the conjugate is to be used in man, then the overriding concerns involve the lack of immunochemical or other side reaction of the carrier and/or the resulting antigen, safety and efficacy--the same considerations that apply to any vaccine intended for human use.

IV. Preparation of Monoclonal Receptors

The lymphocytes employed to form the hybridomas of the present invention may be derived from any mammal, such as a primate, rodent (e.g., mouse or rat), rabbit, guinea pig, cow, dog, sheep, pig or the like. As appropriate, the host may be sensitized by injection of the immunogen, in this instance a haptenic analog-ligand, followed by a booster injection, and then isolation of the spleen.

It is preferred that the myeloma cell line be from the same species as the lymphocytes. Therefore, fused hybrids such as mouse-mouse hybrids [Shulman et al., Nature, 276, 269 (1978)] or rat-rat hybrids [Galfre et al., Nature, 277, 131 (1979)] are typically utilized. However, some rat-mouse hybrids have also been successfully used in forming hybridomas [Goding, "Production of Monoclonal Antibodies by Cell Fusion," in Antibody as a Tool, Marchalonis et al. eds., John Wiley & Sons Ltd., p. 273 (1982)]. Suitable myeloma lines for use in the present invention include MPC-11 (ATCC CRL 167), P3X63-Ag8.653 (ATCC CRL 1580), Sp2/O-Agl4 (ATCC CRL 1581), P3 X 63 Ag8U.1 (ATCC CRL 1597), Y3-Agl.2.3. (deposited at Collection Nationale de Cultures de Microorganisms, Paris, France, number I-078) and P3X63Ag8 (ATCC TIB 9). Murine myeloma line P3X63-Ag8.653 is preferred for use in the present invention.

The hybridoma cells that are ultimately produced may be cultured following usual in vitro tissue culture techniques for such cells as are well known. More preferably, the hybridoma cells are cultured in animals using similarly well known techniques with the monoclonal receptors being obtained from the ascites fluid so generated. The animals used for generation of the ascites fluid are typically BALB/c mice bred in the mouse colony of the Scripps Clinic and Research Foundation, La Jolla, California, however, when animals other than mice are used for preparation of the hybridomas, mice or that animal type can be used for the production of ascites fluid.

In particular, exemplary monoclonal receptors were produced by the standard hybridoma technology of Kohler et al., Nature, 256, 495 (1975). Specifically, BALB/c mice were immunized by intraperitoneal injection with an inoculum of C1 bound to BSA in complete Freund's adjuvant. Three weeks later, the mice were again injected in a like manner. After an additional three weeks, the mice were immunized intravenously with C1 bound to BSA in phosphate buffered saline (PBS) on three consecutive days. The mice were then sacrificed.

The spleens were removed from the mice, pooled and a single cell suspension was made. The spleen cells were then fused with an equal number of P3X63-Ag8.653 myeloma cells in the presence of a cell fusion promoter (polyethylene glycol 2000). The hybridoma that produces a particular monoclonal antibody was selected by seeding the spleen cells in 96-well plates and by growth in Dulbecco's modified Eagle medium (DMEM) containing 10 percent fetal calf serum (FCS), hypoxanthine, aminopterin and thymidine (i.e., HAT medium) which does not support growth of the unfused myeloma cells.

After two to three weeks, the supernatant above the cell clone in each well was sampled and tested by an ELISA assay (enzyme linked immunosorbent assay as described hereafter) for the presence of antibodies against C1. Positive wells were cloned twice by limiting dilution. Those clones that continued to produce C1-specific antibody after two clonings were expanded to produce larger volumes of supernatant fluid.

Alternatively, the monoclonal receptor of the present invention may be produced by introducing, as by injection, the hybridoma into the peritoneal cavity of a mammal such as a mouse. Preferably, as already noted, syngenic or semi-syngenic mammals are used, as in U.S. Pat. No. 4,361,549, the disclosure of which is incorporated herein by reference. The introduction of the hybridoma causes formation of antibody-producing hybridomas after a suitable period of growth, e.g. 1–2 weeks, and results in a high concentration of the receptor being produced that can be recovered from the bloodstream and peritoneal exudate (ascites) of the host mouse. Although the host mice also have normal receptors in their blood and ascites, the concentration of normal receptors is typically only about five percent that of the monoclonal receptor concentration.

The monoclonal receptor present in the hybridoma supernatant can be used without purification or the receptor can be recovered from the ascites or serum of the mouse using standard techniques such as affinity chromatography using AD 169-infected cells bound to an immunosorbant such Sepharose 6B or 4B (Pharmacia Fine Chemicals, Piscataway, NJ), followed by elution from the immunosorbant using an acidic buffer such as glycine hydrochloride at a pH value of about 2.5.

VI. Enzyme-linked Immunosorbent Assay (ELISA)

Assays were performed in flat-bottom polyvinyl microtiter plates (Dynatech, Alexandria, VA). The wells were coated with a solution of C1-analog bound to BSA as the antigen ligand in phosphate buffered saline (PBS) using 50 microliters of solution per well. All ligands were coated at 1 microgram per milliliter. The plates were then incubated overnight at 37° C. in a dry oven. The dried plates were stored at 4° C. until use. Prior to the ELISA assay, dried plates were rehydrated by two washes of 2 minutes each with 10 millimolar (mM) PBS, pH 7.4, containing 0.1 percent polyoxalkylene (20) sorbitan monolaurate (Tween 20) and 0.02 percent Thimerosal (sodium ethylmercurithiosalicylate), (Sigma, St. Louis, MO).

In order to reduce non-specific binding, hybridoma supernatants were diluted 1:2 in washing buffer containing 0.1 percent BSA as diluent. Fifty microliters of diluted hybridoma supernatants were thereafter added to each well and incubated for 1 hour at 4° C. on a gyroshaker to contact the monoclonal antibody-containing supernatant with the bound C1. Following two washes of 2 minutes each, 50 microliters of peroxidase-labeled goat anti-mouse IgG+IgM (Tago, Burlingame, CA), diluted 1:1000, were added to each well, and the reaction mixture was incubated at 4° C. for 1 hour to bind the labeled antibody to bound monoclonal antibody.

The substrate used to assay bound peroxidase activity was prepared just prior to use and consisted of 400 microgram/ml o-phenylenediamine (Sigma, St. Louis, MO) in 80 mM citrate-phosphate buffer, pH 6.0, containing 0.12 percent $H_2O_2$. After two final washes, 50 microliters of substrate solution was added to each well and color was allowed to develop for 15 minutes in the dark. Color development was stopped by adding 25 microliters of 4 molar (M) $H_2SO_4$ to each well and the optical absorbance at 492 nanometers (nm) was measured with a Multiskan ELISA plate reader. Polyclonal antibodies raised to C1 were observed to immunoreact (bind) to the analog-ligand.

The foregoing is intended as illustrative of the present invention but not limiting. Numerous variations and modifications may be effected without departing from true spirit and scope of the invention.

What is claimed is:

1. Antibodies that include an epitope that binds to and thereby stabilizes a tetrahedral carbon intermediate in the hydrolysis of an ester and that are raised in an animal host to a phosphonate of the formula wherein $R_1$ is $R_2$ is H;

$R_4$ is (i) a second bond between the oxygen and central phosphorous atom, (ii) hydrogen or (iii) $C_1$-$C_4$ alkyl; said phosphonate having a conformation that substantially corresponds to the conformation of the tetrahedral carbon intermediate in the hydrolysis of an ester of the formula:

wherein $R_1$, $R_2$, $R_3$ and $R_4$ are as defined above.

2. Antibodies raised in an animal host to a compound of the formula:

3. Antibodies raised in an animal host to a compound of the formula:

4. Antibodies raised in an animal host to a compound of the formula:

5. A compound of the formula:

wherein $R_1$ is

$R_2$ is H;

$R_4$ is (i) a second bond between the oxygen and central phosphorous atom, (ii) hydrogen or (iii) $C_1$–$C_4$ alkyl.

6. A compound of the formula:

7. A compound of the formula:

8. A compound of the formula:

9. A compound of the formula:

10. A compound of the formula:

* * * * *

UNITED STATES PATENT AND TRADEMARK OFFICE
CERTIFICATE OF CORRECTION

PATENT NO. : 4,659,567

DATED : April 21, 1987

INVENTOR(S) : Alfonso Tramontano and Richard A. Lerner

It is certified that error appears in the above-identified patent and that said Letters Patent is hereby corrected as shown below:

Column 8, line 58, in formula delete "$YR_3$" and insert --$OR_3$--

Claim 1, line 6, in formula, delete "$YR_3$" and insert --$OR_3$--

Claim 5, line 3, in formula, delete "$YR_3$" and insert --$OR_3$--

Signed and Sealed this

Thirtieth Day of August, 1988

*Attest:*

DONALD J. QUIGG

*Attesting Officer*  *Commissioner of Patents and Trademarks*

UNITED STATES PATENT AND TRADEMARK OFFICE
CERTIFICATE OF CORRECTION

PATENT NO. : 4,659,567
DATED : April 21, 1987
INVENTOR(S) : Tramontano et al.

It is certified that error appears in the above-identified patent and that said Letters Patent is hereby corrected as shown below:

Column 1, after the heading "DESCRIPTION" before the heading "1. Technical Field", insert the following paragraph:

--This invention was made with government support under Contract No. GM 35318 awarded by the National Institutes of Health. The government has certain rights in the invention.--

Signed and Sealed this

Eighteenth Day of January, 1994

Attest:

BRUCE LEHMAN

Attesting Officer

Commissioner of Patents and Trademarks